United States Patent
Curley et al.

(10) Patent No.: US 9,610,396 B2
(45) Date of Patent: Apr. 4, 2017

(54) SYSTEMS AND METHODS FOR VISUALIZING FLUID ENHANCED ABLATION THERAPY

(71) Applicants: Thermedical, Inc., Waltham, MA (US); Mayo Foundation for Medical Education and Research, Rochester, MN (US)

(72) Inventors: Michael G. Curley, Weston, MA (US); Gregory R. Eberl, Acton, MA (US); Douglas L. Packer, Rochester, MN (US); Malini Madhavan, Rochester, MN (US)

(73) Assignees: Thermedical, Inc., Waltham, MA (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/842,561

(22) Filed: Mar. 15, 2013

(65) Prior Publication Data

US 2014/0275977 A1 Sep. 18, 2014

(51) Int. Cl.
*A61B 18/14* (2006.01)
*A61M 5/00* (2006.01)
(Continued)

(52) U.S. Cl.
CPC ............ *A61M 5/007* (2013.01); *A61B 6/481* (2013.01); *A61B 6/503* (2013.01); *A61B 6/504* (2013.01);
(Continued)

(58) Field of Classification Search
CPC ............ A61B 18/04; A61B 2019/5433; A61B 2018/00982; A61B 2018/044; A61B 2017/00022
(Continued)

(56) References Cited

U.S. PATENT DOCUMENTS

| 4,160,455 A | 7/1979 | Law |
| 4,424,190 A | 1/1984 | Mather, III et al. |

(Continued)

FOREIGN PATENT DOCUMENTS

| CN | 1119127 C | 8/2003 |
| CN | 1525839 A | 9/2004 |

(Continued)

OTHER PUBLICATIONS

David R. Lide (ed)., CRC Handbook of Chemistry and Physics, 87th Edition. 2006. p. 8-81. CRC Press, Florida.
(Continued)

*Primary Examiner* — Elmer Chao
(74) *Attorney, Agent, or Firm* — Nutter McClennen & Fish LLP

(57) ABSTRACT

Systems and methods for visualizing fluid enhanced ablation therapy are described herein. In one embodiment, a method for ablating tissue is provided that includes inserting an elongate body into a tissue volume, heating an imageable fluid within the elongate body to transform the imageable fluid into an imageable therapeutic fluid, delivering the imageable therapeutic fluid into the tissue volume to deliver a therapeutic dose of thermal energy to the tissue volume, and imaging the tissue volume to determine the extent of the tissue volume containing the imageable therapeutic fluid. The imageable therapeutic fluid can indicate the extent of the tissue volume that has received the therapeutic dose of thermal energy.

17 Claims, 7 Drawing Sheets

(51) Int. Cl.
   *A61B 6/00* (2006.01)
   *A61B 18/04* (2006.01)
   *A61B 8/08* (2006.01)
   A61B 5/055 (2006.01)
   G01R 33/48 (2006.01)
   A61B 18/00 (2006.01)
   A61B 90/00 (2016.01)

(52) U.S. Cl.
   CPC .............. *A61B 6/507* (2013.01); *A61B 8/481* (2013.01); *A61B 18/04* (2013.01); *A61B 18/1477* (2013.01); *A61B 5/055* (2013.01); *A61B 6/487* (2013.01); *A61B 6/501* (2013.01); *A61B 2018/00083* (2013.01); *A61B 2018/00577* (2013.01); *A61B 2018/046* (2013.01); *A61B 2018/1472* (2013.01); *A61B 2090/374* (2016.02); *A61B 2090/376* (2016.02); *G01R 33/4808* (2013.01)

(58) Field of Classification Search
   USPC ................. 606/41, 14, 15; 607/99, 105, 113
   See application file for complete search history.

(56) References Cited

U.S. PATENT DOCUMENTS

| | | |
|---|---|---|
| 5,271,413 A | 12/1993 | Dalamagas et al. |
| 5,336,222 A | 8/1994 | Durgin, Jr. et al. |
| 5,403,311 A | 4/1995 | Abele et al. |
| 5,409,487 A | 4/1995 | Jalbert et al. |
| 5,431,648 A | 7/1995 | Lev |
| 5,431,649 A | 7/1995 | Mulier et al. |
| 5,449,380 A | 9/1995 | Chin |
| 5,456,682 A | 10/1995 | Edwards et al. |
| 5,458,597 A | 10/1995 | Edwards et al. |
| 5,462,521 A | 10/1995 | Brucker et al. |
| 5,472,441 A | 12/1995 | Edwards et al. |
| 5,496,271 A | 3/1996 | Burton et al. |
| 5,522,815 A | 6/1996 | Durgin, Jr. et al. |
| 5,545,195 A | 8/1996 | Lennox et al. |
| 5,549,559 A | 8/1996 | Eshel |
| 5,653,692 A | 8/1997 | Masterson et al. |
| 5,728,143 A | 3/1998 | Gough et al. |
| 5,735,846 A | 4/1998 | Panescu et al. |
| 5,800,482 A | 9/1998 | Pomeranz et al. |
| 5,827,269 A | 10/1998 | Saadat |
| 5,891,094 A | 4/1999 | Masterson et al. |
| 5,891,134 A | 4/1999 | Goble et al. |
| 5,954,719 A | 9/1999 | Chen et al. |
| 5,964,791 A | 10/1999 | Bolmsjo |
| 6,024,743 A | 2/2000 | Edwards |
| 6,030,379 A | 2/2000 | Panescu et al. |
| 6,032,077 A | 2/2000 | Pomeranz |
| 6,045,549 A | 4/2000 | Smethers et al. |
| 6,056,746 A | 5/2000 | Goble et al. |
| 6,071,280 A | 6/2000 | Edwards et al. |
| 6,112,123 A * | 8/2000 | Kelleher et al. ............... 607/98 |
| 6,119,041 A | 9/2000 | Pomeranz et al. |
| 6,139,570 A | 10/2000 | Saadat et al. |
| 6,139,571 A | 10/2000 | Fuller et al. |
| 6,179,803 B1 | 1/2001 | Edwards et al. |
| 6,208,881 B1 | 3/2001 | Champeau |
| 6,233,490 B1 | 5/2001 | Kasevich |
| 6,238,393 B1 | 5/2001 | Mulier et al. |
| 6,272,370 B1 * | 8/2001 | Gillies et al. ............... 600/411 |
| 6,302,904 B1 | 10/2001 | Wallsten et al. |
| 6,315,777 B1 | 11/2001 | Comben |
| 6,328,735 B1 * | 12/2001 | Curley et al. ............... 606/41 |
| 6,337,994 B1 | 1/2002 | Stoianovici et al. |
| 6,358,273 B1 | 3/2002 | Strul et al. |
| 6,405,067 B1 | 6/2002 | Mest et al. |
| 6,409,722 B1 | 6/2002 | Hoey et al. |
| 6,443,947 B1 | 9/2002 | Marko et al. |
| 6,463,332 B1 | 10/2002 | Aldrich |
| 6,464,694 B1 | 10/2002 | Massengill |
| 6,468,274 B1 | 10/2002 | Alleyne et al. |
| 6,475,213 B1 | 11/2002 | Whayne et al. |
| 6,477,396 B1 | 11/2002 | Mest et al. |
| 6,494,902 B2 | 12/2002 | Hoey et al. |
| 6,529,756 B1 | 3/2003 | Phan et al. |
| 6,564,096 B2 | 5/2003 | Mest |
| 6,565,561 B1 | 5/2003 | Goble et al. |
| 6,603,997 B2 | 8/2003 | Doody |
| 6,620,155 B2 | 9/2003 | Underwood et al. |
| 6,641,580 B1 | 11/2003 | Edwards et al. |
| 6,669,685 B1 | 12/2003 | Rizoiu et al. |
| 6,678,552 B2 | 1/2004 | Pearlman |
| 6,702,810 B2 | 3/2004 | McClurken et al. |
| 6,752,802 B1 | 6/2004 | Isenberg et al. |
| 6,772,012 B2 | 8/2004 | Ricart et al. |
| 6,814,730 B2 | 11/2004 | Li |
| 6,904,303 B2 | 6/2005 | Phan et al. |
| 6,972,014 B2 | 12/2005 | Eum et al. |
| 7,001,378 B2 | 2/2006 | Yon et al. |
| 7,070,597 B2 | 7/2006 | Truckai et al. |
| 7,101,369 B2 | 9/2006 | van der Welde |
| 7,160,259 B2 | 1/2007 | Tardy et al. |
| 7,179,256 B2 | 2/2007 | Mest |
| 7,207,989 B2 | 4/2007 | Pike, Jr. et al. |
| 7,244,254 B2 | 7/2007 | Brace et al. |
| 7,270,659 B2 | 9/2007 | Ricart et al. |
| 7,311,703 B2 | 12/2007 | Turovskiy et al. |
| 7,387,625 B2 | 6/2008 | Hovda et al. |
| 7,387,630 B2 | 6/2008 | Mest |
| 7,412,273 B2 | 8/2008 | Jais et al. |
| 7,416,552 B2 | 8/2008 | Paul et al. |
| 7,559,905 B2 | 7/2009 | Kagosaki et al. |
| 7,604,634 B2 | 10/2009 | Hooven |
| 7,879,030 B2 | 2/2011 | Paul et al. |
| 7,938,822 B1 | 5/2011 | Berzak et al. |
| 7,951,143 B2 | 5/2011 | Wang et al. |
| 7,993,335 B2 | 8/2011 | Rioux et al. |
| 8,128,620 B2 | 3/2012 | Wang et al. |
| 8,128,621 B2 | 3/2012 | Wang et al. |
| 8,273,082 B2 | 9/2012 | Wang et al. |
| 8,287,531 B2 | 10/2012 | Mest |
| 8,333,762 B2 | 12/2012 | Mest et al. |
| 8,369,922 B2 | 2/2013 | Paul et al. |
| 8,439,907 B2 | 5/2013 | Auth et al. |
| 8,444,638 B2 | 5/2013 | Woloszko et al. |
| 8,449,535 B2 | 5/2013 | Deno et al. |
| 8,591,507 B2 | 11/2013 | Kramer et al. |
| 8,663,226 B2 | 3/2014 | Germain |
| 8,700,133 B2 | 4/2014 | Hann |
| 8,702,697 B2 | 4/2014 | Curley |
| 8,755,860 B2 | 6/2014 | Paul et al. |
| 8,758,349 B2 | 6/2014 | Germain et al. |
| 8,864,760 B2 | 10/2014 | Kramer et al. |
| 8,945,121 B2 | 2/2015 | Curley |
| 9,033,972 B2 | 5/2015 | Curley |
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 2001/0031946 A1 | 10/2001 | Walker et al. |
| 2002/0120259 A1 | 8/2002 | Lettice et al. |
| 2002/0123749 A1 | 9/2002 | Jain |
| 2002/0183735 A1 | 12/2002 | Edwards et al. |
| 2003/0109871 A1 | 6/2003 | Johnson et al. |
| 2003/0120271 A1 | 6/2003 | Burnside et al. |
| 2004/0006336 A1 | 1/2004 | Swanson |
| 2004/0116922 A1 | 6/2004 | Hovda et al. |
| 2004/0220559 A1 | 11/2004 | Kramer et al. |
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0165391 A1 | 7/2005 | Maguire et al. |
| 2005/0187599 A1 | 8/2005 | Sharkey et al. |
| 2005/0192652 A1 | 9/2005 | Cioanta et al. |
| 2005/0245923 A1 | 11/2005 | Christopherson et al. |
| 2005/0267552 A1 | 12/2005 | Conquergood et al. |

(56) References Cited

U.S. PATENT DOCUMENTS

| | | |
|---|---|---|
| 2006/0085054 A1 | 4/2006 | Zikorus et al. |
| 2006/0118127 A1 | 6/2006 | Chinn |
| 2006/0216275 A1 | 9/2006 | Mon |
| 2006/0259024 A1 | 11/2006 | Turovskiy et al. |
| 2006/0276780 A1 | 12/2006 | Brace et al. |
| 2006/0287650 A1 | 12/2006 | Cao et al. |
| 2007/0032786 A1 | 2/2007 | Francischelli |
| 2007/0185483 A1 | 8/2007 | Butty et al. |
| 2007/0219434 A1 | 9/2007 | Abreu |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0154258 A1 | 6/2008 | Chang et al. |
| 2008/0161788 A1 | 7/2008 | Dando et al. |
| 2008/0161797 A1 | 7/2008 | Wang et al. |
| 2008/0167650 A1 | 7/2008 | Joshi et al. |
| 2008/0275438 A1 | 11/2008 | Gadsby et al. |
| 2008/0275440 A1 | 11/2008 | Kratoska et al. |
| 2008/0288038 A1 | 11/2008 | Paul et al. |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1 | 7/2009 | Luttich |
| 2009/0254083 A1 | 10/2009 | Wallace et al. |
| 2010/0030098 A1 | 2/2010 | Fojtik |
| 2010/0094272 A1 | 4/2010 | Rossetto et al. |
| 2010/0198056 A1* | 8/2010 | Fabro et al. ............... 600/424 |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1* | 6/2011 | Connor et al. ............. 600/424 |
| 2011/0160726 A1 | 6/2011 | Ingle |
| 2011/0184603 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2012/0108938 A1 | 5/2012 | Kauphusman et al. |
| 2012/0130381 A1 | 5/2012 | Germain |
| 2012/0265190 A1 | 10/2012 | Curley et al. |
| 2012/0265199 A1 | 10/2012 | Curley |
| 2012/0265200 A1 | 10/2012 | Curley |
| 2012/0265276 A1 | 10/2012 | Curley |
| 2012/0277737 A1* | 11/2012 | Curley ........................ 606/33 |
| 2012/0310230 A1 | 12/2012 | Willis |
| 2014/0052117 A1 | 2/2014 | Curley |
| 2014/0188106 A1 | 7/2014 | Curley |
| 2014/0276743 A1 | 9/2014 | Curley |
| 2014/0350542 A1 | 11/2014 | Kramer et al. |
| 2015/0066025 A1 | 3/2015 | Curley |
| 2015/0223882 A1 | 8/2015 | Curley |
| 2015/0351823 A1 | 12/2015 | Curley |
| 2015/0359582 A1 | 12/2015 | Curley et al. |

FOREIGN PATENT DOCUMENTS

| | | |
|---|---|---|
| CN | 1897885 A | 1/2007 |
| CN | 101209217 A | 7/2008 |
| CN | 101578073 A | 11/2009 |
| CN | 201642316 U | 11/2010 |
| CN | 101999931 A | 4/2011 |
| EP | 0 895 756 A1 | 2/1999 |
| EP | 0 908 156 A1 | 4/1999 |
| EP | 1 033 107 A1 | 9/2000 |
| EP | 2 042 112 A2 | 4/2009 |
| EP | 2 430 996 A2 | 3/2012 |
| JP | 10-505268 A | 5/1998 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/32186 A1 | 7/1999 |
| WO | 02/089686 A1 | 11/2002 |
| WO | 2005/048858 A1 | 6/2005 |
| WO | 2005/089663 A1 | 9/2005 |
| WO | 2006/055658 A1 | 5/2006 |
| WO | 2006/095171 A1 | 9/2006 |
| WO | 2006/102471 A2 | 9/2006 |
| WO | 2006/103951 A1 | 10/2006 |
| WO | 2007/080578 A2 | 7/2007 |
| WO | 2010/002733 A1 | 1/2010 |
| WO | 2010/151619 A2 | 12/2010 |
| WO | 2012/071058 A1 | 5/2012 |

OTHER PUBLICATIONS

International Search Report and Written Opinion for Application No. PCT/US2012/033203, issued Sep. 21, 2012. (23 pages).

International Search Report and Written Opinion for Application No. PCT/US2012/033213, issued Sep. 21, 2012. (17 pages).

International Search Report and Written Opinion for Application No. PCT/US2012/033216, issued Sep. 21, 2012. (17 pages).

International Search Report and Written Opinion for Application No. PCT/US2012/033327, issued Sep. 21, 2012. (14 pages).

International Search Report and Written Opinion for Application No. PCT/US2012/033332, issued Sep. 21, 2012. (20 pages).

Nath et al., Prog. Card. Dis. 37(4):185-205 (1995).

Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.

Sapareto et al., Int. J Rad. One. Biol. Phys. 10(6):787-800 (1984).

Brace CL. Microwave tissue ablation: biophysics, technology, and applications.; Crit Rev Biomed Eng. 2010;38 (1):65-78.

International Search Report and Written Opinion for Application No. PCT/US2013/053977, issued Nov. 14, 2013. (20 pages).

International Search Report and Written Opinion for Application No. PCT/US2014/024731, mailed Jul. 21, 2014 (39 pages).

Extended European Search Report and Written Opinion for Application No. 12771601.7 issued Oct. 27, 2014 (7 pages).

Extended European Search Report and Written Opinion for EP 12771331.1 dated Sep. 25, 2014 (6 pages).

Extended Search Report and Written Opinion for EP 12 77 0537 dated Oct. 10, 2014 (6 pages).

Extended Search Report and Written Opinion for EP 12 77 0631.5 dated Oct. 1, 2014 (6 Pages).

Extended Search Report and Written Opinion for EP 12 77 1876 dated Oct. 13, 2014 (6 pages).

Chinese Office Action for Application No. 201280028609.9, issued May 27, 2015. (22 pages).

Chinese Office Action for Application No. 201280028620.5, issued May 27, 2015. (26 pages).

Chinese Office Action for Application No. 201280028611.6, issued Jul. 29, 2015. (23 pages).

Chinese Office Action for Application No. 201280028621.X, issued Jul. 31, 2015. (18 pages).

U.S. Appl. No. 14/688,790, filed Apr. 16, 2015, Methods and Devices for Fluid Enhanced Microwave Ablation Therapy.

U.S. Appl. No. 14/826,549, filed Aug. 14, 2015, Methods and Devices for Heating Fluid in Fluid Enhanced Ablation Therapy.

U.S. Appl. No. 14/826,563, filed Aug. 14, 2015, Methods and Devices for Use of Degassed Fluids With Fluid Enhanced Ablation Devices.

Chinese Office Action for Application No. 201380053690.0, issued Sep. 30, 2016. (17 pages).

Extended European Search Report and Search Opinion for Application No. 13829821.1 issued Mar. 17, 2016 (7 pages).

Japanese Office Action for Application No. 2014-505263, mailed Jan. 26, 2016 (4 pages).

Japanese Office Action for Application No. 2014-505266, mailed Feb. 23, 2016 (7 pages).

Young, S.T., et al., An instrument using variation of resistance to aid in needle tip insertion in epidural block in monkeys. Med Instrum. Oct. 1987;21(5):266-8. Abstract Only.

\* cited by examiner

SYSTEMS AND METHODS FOR VISUALIZING FLUID ENHANCED ABLATION THERAPY

FIELD

The present invention relates generally to fluid enhanced ablation therapy, and more particularly, to systems and methods for visualizing the flow of fluid introduced during fluid enhanced ablation therapy.

BACKGROUND

Fluid enhanced ablation therapy involves the introduction of a fluid into a volume of tissue to deliver a therapeutic dose of energy in order to destroy tissue. The fluid can act as a therapeutic agent delivering thermal energy into the tissue volume—thermal energy supplied from the fluid itself (e.g., a heated fluid) or from an ablation element that provides thermal energy using, e.g., radio frequency (RF) electrical energy, microwave or light wave electromagnetic energy, ultrasonic vibrational energy, etc. This therapy can be applied to a variety of procedures, including the destruction of tumors.

One example of fluid enhanced ablation therapy is the SERF™ ablation technique (Saline Enhanced Radio Frequency™ ablation) described in U.S. Pat. No. 6,328,735, which is hereby incorporated by reference in its entirety. Using the SERF ablation technique, saline is passed through a needle and heated, and the heated fluid is delivered into a target volume of tissue surrounding the needle. In addition, RF electrical current is simultaneously passed through the tissue between an emitter electrode positioned on the needle and a remotely located return electrode. The saline acts as a therapeutic agent to deliver its thermal energy to the target volume of tissue via convection, and the RF electrical energy can act to supplement and/or replenish the thermal energy of the fluid that is lost as it moves through the tissue. The delivery of thermal energy via the movement of fluid through tissue can allow a greater volume of tissue to be treated with a therapeutic dose of ablative energy than is possible with other known techniques. The therapy is usually completed once the target volume of tissue reaches a desired therapeutic temperature, or otherwise receives a therapeutic dose of energy.

A common challenge in fluid enhanced ablation therapy is determining the extent of the target volume of tissue that has received a therapeutic dose of thermal energy. Known techniques for monitoring therapy progress include measuring the temperature of various portions of the target volume of tissue directly. Exemplary devices and methods for conducting such monitoring are described in U.S. Pat. Pub. No. 2012/0277737, which is hereby incorporated by reference in its entirety.

However, measuring the temperature of various portions of the target volume of tissue is not necessarily an effective technique for monitoring therapy progress. This is because it is often impractical to include more than a few temperature sensors on a single device, and the sensors can only report the temperature of the target volume of tissue in their immediate location. As a result, it can be difficult to monitor the overall shape of the treated volume of tissue.

Still further, misplacement of the needle or other fluid introduction device, or adjacent anatomical features that have high blood flow (e.g., capillaries, veins, etc.) can result in undesired and unexpected fluid flow. This unexpected fluid flow can direct therapeutic energy in an unexpected manner, thereby altering the shape and size of the treated volume of tissue that has received a therapeutic dose of thermal energy. Techniques for remotely monitoring the temperature of the target volume of tissue can report that the temperature is not rising as expected, but may not show where the heated fluid is flowing to and what the altered treated volume of tissue looks like.

Accordingly, there is a need in the art for improved systems and methods for monitoring fluid enhanced ablation therapy.

SUMMARY

The present invention generally provides systems and methods for directly visualizing fluid enhanced ablation therapy. The systems and methods described herein generally include visualizing the flow of an imageable therapeutic fluid in a fluid enhanced ablation therapy procedure and correlating the visualized fluid flow with the shape and size of a volume of tissue that has received a therapeutic dose of thermal energy. In some cases, the imageable therapeutic fluid can be, e.g., a heated mix of one or more fluids (e.g., saline) that includes a contrast agent that can be used to visualize the flow of the therapeutic fluid. The visualized fluid flow can in some cases directly indicate the volume of tissue that has received a therapeutic dose of thermal energy or, in other cases, can indicate that a certain portion of the volume of tissue has received a therapeutic dose of thermal energy.

In one aspect, a method for ablating tissue is provided that includes inserting an elongate body into a tissue volume, heating an imageable fluid within the elongate body to transform the imageable fluid into an imageable therapeutic fluid, delivering the imageable therapeutic fluid into the tissue volume to deliver a therapeutic dose of thermal energy to the tissue volume, and imaging the tissue volume to determine the extent of the tissue volume containing the imageable therapeutic fluid. The imageable therapeutic fluid can indicate the extent of the tissue volume that has received the therapeutic dose of thermal energy.

In another embodiment, the method can include inserting an elongate body having an ablation element disposed thereon into a tissue volume. The method can further include heating an imageable fluid within the elongate body to transform the imageable fluid into an imageable therapeutic fluid, and delivering energy to the ablation element on the elongate body. The energy and the imageable therapeutic fluid can be simultaneously delivered into the volume of tissue to deliver a therapeutic dose of thermal energy to the tissue volume. The method can further include imaging the tissue volume to determine the extent of the tissue volume containing the imageable therapeutic fluid, wherein the imageable therapeutic fluid can indicate the extent of the tissue volume that has received the therapeutic dose of thermal energy.

The systems and methods described herein can have a number of additional features and/or modifications, all of which are considered within the scope of the present invention. For example, a variety of fluids can be used in the systems and methods described herein. In certain embodiments, the imageable fluid can include saline and a contrast agent to aid in visualizing the flow of the imageable fluid. The saline and contrast agent can be mixed together in a variety of proportions, either prior to use or instantaneously as the imageable fluid is delivered to the elongate body. In some embodiments, a ratio of saline to contrast agent can be about 1:1. In other embodiments, the ratio of saline to contrast agent can be about 10:1, while in still other embodiments the ratio of saline to contrast agent can be about 20:1. A number of different contrast agents can be employed with the systems and methods of the present invention, so long as they do not adversely impact the safety or effectiveness of the therapy procedure, as described in more detail below. In some embodiments, the contrast agent can be a water soluble contrast agent, and more preferably an iodinated water soluble contrast agent, such as iohexol.

In some embodiments, it can be important for the imageable therapeutic fluid utilized to have a heat capacity that is close to, or greater than, the heat capacity of the tissue itself. The imageable therapeutic fluid can act by exchanging thermal energy with tissue, therefore using a fluid with a heat capacity close to, or greater than, the heat capacity of the tissue can ensure that the imageable therapeutic fluid does not excessively lose its stored energy to the tissue as it heats the tissue. In some embodiments, for example, a heat capacity of the imageable therapeutic fluid can be greater than about 2 J/ml-° C., and more preferably greater than about 4 J/ml-° C.

A variety of different medical imaging technologies can be utilized to image the tissue volume to determine the extent of the tissue volume containing the imageable fluid. In some embodiments, for example, the tissue volume can be imaged using fluoroscopy, computed tomography (CT) scan, computer axial tomography (CAT) scan, magnetic resonance imaging (MRI), or ultrasound. The medical imaging technology utilized can, in some embodiments, be selected based on the contrast agent used in the imageable therapeutic fluid. For example, if iohexol is used as the contrast agent, the tissue can be imaged using computed tomography (CT) scanning, fluoroscopy, or some other form of X-ray imaging that is sensitive to iohexol.

Heating of the imageable fluid can be accomplished in a variety of manners. In certain embodiments, the imageable fluid can be heated by a heating element disposed within the elongate body. A number of different heating elements can be employed, including radio frequency (RF), laser, microwave, and resistive electrical heating elements. Further details on exemplary heating elements that can be used in the systems and methods described herein can be found in U.S. Pat. Pub. No. 2012/0265190, which is hereby incorporated by reference in its entirety.

As mentioned above, the visualized fluid flow in the tissue volume can indicate the extent of the tissue volume that has received the therapeutic dose of thermal energy. In some embodiments, a ratio of a linear dimension of a portion of the tissue volume containing the imageable therapeutic fluid to a linear dimension of a portion of the tissue volume that has received the therapeutic dose of thermal energy can be about 1:1. That is, the visualized fluid flow can directly correlate to the size of the treated volume of tissue. However, the correlation between the portion of the tissue volume containing the imageable therapeutic fluid to the portion of the tissue volume that has been treated need not be 1:1. For example, in some embodiments, a ratio of a linear dimension of a portion of the tissue volume containing the imageable therapeutic fluid to a linear dimension of a portion of the tissue volume that has received the therapeutic dose of thermal energy can be about 3:2. In other embodiments, a ratio of a linear dimension of a portion of the tissue volume containing the imageable therapeutic fluid to a linear dimension of a portion of the tissue volume that has received the therapeutic dose of thermal energy can be about 2:1. In still other embodiments, a ratio of a linear dimension of a portion of the tissue volume containing the imageable therapeutic fluid to a linear dimension of a portion of the tissue volume that has received the therapeutic dose of thermal energy can be about 5:1. Still further, in some embodiments, a ratio of a linear dimension of a portion of the tissue volume containing the imageable therapeutic fluid to a linear dimension of a portion of the tissue volume that has received the therapeutic dose of thermal energy can be about 10:1.

In certain embodiments, the relationship between the size of a portion of the tissue volume containing the imageable therapeutic fluid and the size of a portion of the tissue volume that has received a therapeutic dose of thermal energy can be described by a mathematical relationship. In some embodiments, for example, the method can include evaluating a mathematical model using a dimension of the imaged tissue volume containing the imageable therapeutic fluid to determine a dimension of the tissue volume that has received the therapeutic dose of thermal energy. In other embodiments, a ratio between the dimension of the tissue volume that has received the therapeutic dose of thermal energy calculated by the mathematical model and the dimension of the imaged tissue volume containing the imageable therapeutic fluid can be about 2:3. Of course, this calculated value can vary based on the mathematical model derived from, for example, the therapy operating parameters, tissue type, size and shape of the tissue volume, nearby sources of blood flow, etc.

The ablation element disposed on the elongate body can utilize a variety of types of therapeutic energy. For example, in some embodiments the ablation element can include a source of electromagnetic energy. Exemplary sources of electromagnetic energy can include, in various embodiments, RF electrical energy, laser light energy, and microwave electrical energy. In other embodiments, the ablation element can include a source of ultrasonic energy.

In another aspect, a system for delivering fluid enhanced ablation therapy is provided that includes an elongate body having proximal and distal ends, an inner lumen extending through the elongate body, at least one outlet port formed in the elongate body, and at least one ablation element positioned along the length of a distal portion of the elongate body. The system can further include an imageable fluid source in communication with the inner lumen of the elongate body, the imageable fluid source including saline and a contrast agent. The system can further include a heating element disposed within the inner lumen of the elongate body and configured to heat the imageable fluid to transform the imageable fluid into an imageable therapeutic fluid that can flow through the at least one outlet port and be delivered to tissue surrounding the at least one ablation element.

All of the variations and modifications discussed above can be included in a system according to the teachings of the present invention. For example, in some embodiments a heat capacity of the imageable fluid can be greater than about 2 J/ml-° C., and more preferably greater than about 4 J/ml-° C. In other embodiments, a ratio of saline to contrast agent can be about 1:1. In still other embodiments, a ratio of saline to contrast agent can be about 10:1. In yet other embodiments, a ratio of saline to contrast agent can be about 20:1. Furthermore, a variety of contrast agents can be used in the imageable fluid. In some embodiments, the contrast agent can be iohexol.

The ablation element positioned along the length of a distal portion of the elongate body can be configured to deliver a variety of types of energy into the tissue surrounding the elongate body. For example, in some embodiments, the ablation element can be configured to deliver energy selected from the group consisting of electromagnetic energy, radio frequency energy, laser energy, microwave energy, and ultrasonic energy.

The systems and methods described herein can provide a number of advantages over prior art systems and methods for monitoring fluid enhanced ablation therapy. In particular, the systems and methods described herein can allow for the direct visualization of the flow of an imageable therapeutic fluid as it delivers thermal energy within a target tissue volume. The expansion over time of a portion of the tissue volume containing the imageable therapeutic fluid can be monitored to ensure that fluid is not flowing in an undesirable or unexpected manner, and the size of the portion of the tissue volume containing the visualized therapeutic fluid can be used to indicate the size of the portion of the tissue volume that has received a therapeutic dose of thermal energy. Accordingly, the systems and methods described herein can provide a far more robust and detailed view of the progress of a fluid enhanced ablation therapy procedure.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Figure 1:
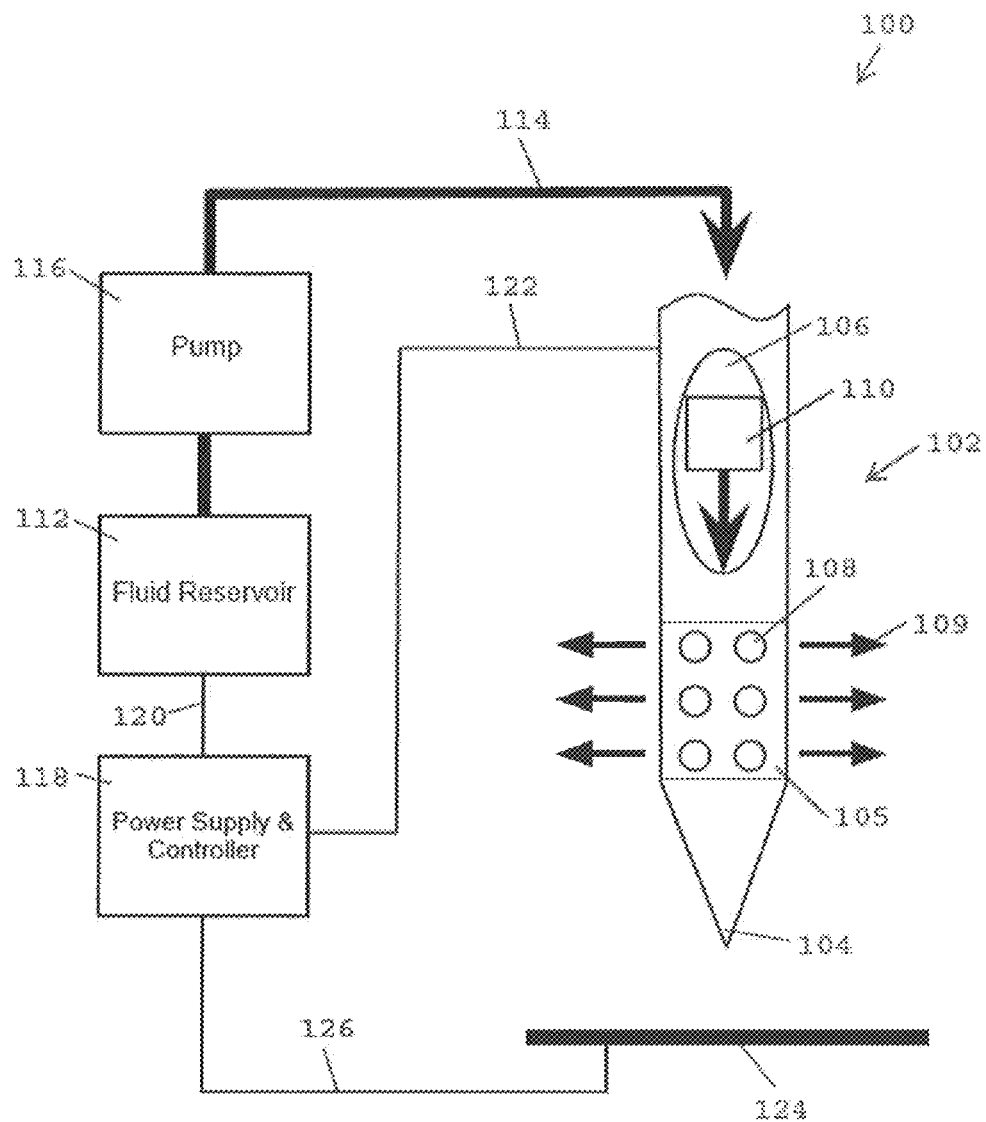
FIG. 1 is a diagram of one embodiment of a fluid enhanced ablation therapy system.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is generally directed to systems and methods for visualizing fluid enhanced ablation therapy and, in particular, to systems and methods for visualizing the expansion over time of a proportion of a volume of tissue that has received a therapeutic dose of thermal energy (i.e., visualizing the expansion of a therapeutic temperature front as it encompasses a greater volume of tissue over time). The systems and methods described herein generally include visualizing the flow of an imageable therapeutic fluid in a fluid enhanced ablation therapy procedure and correlating the visualized flow with the shape and size of a volume of tissue that has received a therapeutic dose of thermal energy. In some cases, the imageable therapeutic fluid can be, e.g., a heated mix of saline and a contrast agent that can aid in visualizing the flow of the therapeutic fluid. The visualized fluid can in some cases directly indicate the volume of tissue that has received a therapeutic dose of thermal energy or, in other cases, can indicate that a certain portion of the volume of tissue containing the imageable therapeutic fluid has received a therapeutic dose of thermal energy. The systems and methods described herein provide unique advantages over known methods for monitoring fluid enhanced ablation therapy, including, for example, the ability to directly visualize the flow of an imageable therapeutic fluid within a patient's body to monitor the progress of a therapeutic procedure.

Fluid enhanced ablation therapy, as mentioned above, is defined by passing a fluid into tissue to act as a therapeutic agent and deliver thermal energy into the tissue. The thermal energy can be provided from the fluid itself (e.g., by using heated fluid), by delivering therapeutic energy from an ablation element (e.g., an RF electrode), or a combination of the two. The delivery of therapeutic energy into tissue causes hyperthermia in the tissue, ultimately resulting in necrosis. This temperature-induced selective destruction of tissue can be utilized to treat a variety of conditions including tumors, fibroids, cardiac dysrhythmias (e.g., ventricular tachycardia, etc.), and others.

The SERF™ ablation technique (Saline Enhanced Radio Frequency™ ablation) described in U.S. Pat. No. 6,328,735 and incorporated by reference above, delivers fluid heated to a therapeutic temperature into tissue along with ablative energy. The heated fluid acts as a therapeutic agent by flowing through the extracellular space of the treatment tissue and increasing the heat transfer through the tissue significantly. In particular, the flowing heated fluid convects thermal energy into the target tissue. The thermal energy can be supplied from the heated fluid itself, and the ablation energy source can act to replenish thermal energy lost from the fluid as it moves through tissue. Furthermore, the fluid can serve to constantly hydrate the tissue and prevent any tissue charring and associated impedance rise near the ablation element, as described in more detail below.

Fluid enhanced ablation therapy can have a number of advantages over prior art ablation techniques, such as conventional RF ablation. For example, conventional RF ablation often overheats the tissue located adjacent to the emitter electrode because the heat cannot be efficiently transported away from the electrode. This overheating can cause charring of the tissue and an associated rise in impedance that can effectively terminate the therapy. During fluid enhanced ablation therapy, in contrast, the therapeutically heated fluid can convect heat deeper into the target tissue, thereby reducing tissue charring and the associated impedance change of the tissue. Further, because the fluid is heated to a therapeutic level, it does not act as a heat sink that draws down the temperature of the surrounding tissue. Instead, the fluid itself acts as the therapeutic agent delivering thermal energy into the tissue and the RF energy can act to counter the loss of thermal energy from the fluid as it moves through the tissue. Therefore, the concurrent application of RF energy and injection of heated fluid into the tissue can eliminate the desiccation and/or vaporization of tissue adjacent to the electrode, maintain the effective tissue impedance, and increase the thermal transport within the tissue being heated with RF energy. The total volume of tissue that can be heated to therapeutic temperatures is thereby increased when compared to, e.g., conventional RF ablation.

In addition, fluid enhanced ablation therapy devices have a greater number of parameters that can be varied to adjust the shape of the treated volume of tissue. For example, when using the SERF ablation technique, an operator or control system can modify parameters such as fluid temperature (e.g., from about 40° C. to about 80° C.), fluid flow rate (e.g., from about 0 ml/min to about 20 ml/min), RF power (e.g., from about 0 W to about 100 W), and duration of treatment (e.g., from about 0 min to about 10 min) to adjust the temperature profile within the target volume of tissue. Different electrode configurations can also be used to vary the treatment. For example, an emitter electrode can be configured as a continuous cylindrical band around a needle or other elongate body, or the electrode can be formed in other geometries, such as spherical or helical. The electrode can form a continuous surface area, or it can have a plurality of discrete portions.

Figure 2:
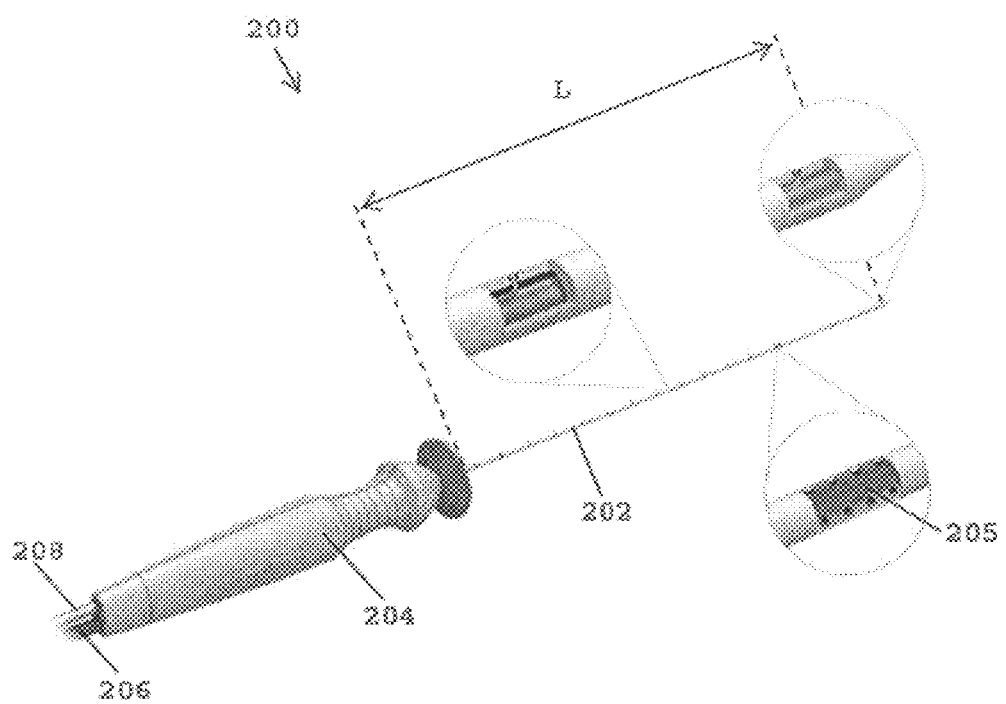
FIG. 2 is a perspective view of one embodiment of a medical device having an elongate body for use in fluid enhanced ablation therapy.

FIG. 1 illustrates a diagram of one embodiment of a fluid enhanced ablation system 100. The system includes an elongate body 102 configured for insertion into a target volume of tissue. The elongate body can have a variety of shapes and sizes according to the geometry of the target tissue. Further, the particular size of the elongate body can depend on a variety of factors including the type and location of tissue to be treated, the size of the tissue volume to be treated, etc. By way of example only, in one embodiment, the elongate body can be a thin-walled stainless steel needle between about 16- and about 18-gauge (i.e., an outer diameter of about 1.27 mm to about 1.65 mm), and having a length L (e.g., as shown in FIG. 2) that is approximately 25 cm. The elongate body 102 can include a pointed distal tip 104 configured to puncture tissue to facilitate introduction of the device into a target volume of tissue, however, in other embodiments the tip can be blunt and can have various other configurations. The elongate body 102 can be formed from a conductive material such that the elongate body can conduct electrical energy along its length to one or more ablation elements located along a distal portion of the elongate body. Mono-polar emitter electrode 105 is an example of an ablation element capable of delivering RF energy from the elongate body.

In some embodiments, the emitter electrode 105 can be a portion of the elongate body 102. For example, the elongate body 102 can be coated in an insulating material along its entire length except for the portion representing the emitter electrode 105. More particularly, in one embodiment, the elongate body 102 can be coated with 1.5 mil of the fluoropolymer Xylan™ 8840. In other embodiments, different coatings can be used in place of, or in conjunction with, the fluoropolymer coating. For example, in certain embodiments, 1 mil of Polyester shrink tubing can be disposed over the Xylan coating. The electrode 105 can have a variety of lengths and shape configurations. In one embodiment, the electrode 105 can be a 4 mm section of a tubular elongate body that is exposed to surrounding tissue. Further, the electrode 105 can be located anywhere along the length of the elongate body 105 (and there can also be more than one electrode disposed along the length of the elongate body). In one embodiment, the electrode can be located adjacent to the distal tip 104. In other embodiments, the elongate body can be formed from an insulating material, and the electrode can be disposed around the elongate body or between portions of the elongate body.

In other embodiments, the electrode can be formed from a variety of other materials suitable for conducting current. Any metal or metal salt may be used. Aside from stainless steel, exemplary metals include platinum, gold, or silver, and exemplary metal salts include silver/silver chloride. In one embodiment, the electrode can be formed from silver/silver chloride. It is known that metal electrodes assume a voltage potential different from that of surrounding tissue and/or liquid. Passing a current through this voltage difference can result in energy dissipation at the electrode/tissue interface, which can exacerbate excessive heating of the tissue near the electrodes. One advantage of using a metal salt such as silver/silver chloride is that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can reduce excessive energy generation at the tissue interface and thereby produce a more desirable therapeutic temperature profile, even where there is no liquid flow about the electrode.

The electrode 105 or other ablation element can include one or more outlet ports 108 that are configured to deliver fluid from an inner lumen 106 extending through the elongate body 102 into surrounding tissue (as shown by arrows 109). Alternatively, the electrode 105 can be positioned near one or more outlet ports 108 formed in the elongate body 102. In many embodiments, it can be desirable to position the electrode adjacent to the one or more outlet ports to maximize the effect of the flowing fluid on the therapy. The outlet ports 108 can be formed in a variety of sizes, numbers, and pattern configurations. In addition, the outlet ports 108 can be configured to direct fluid in a variety of directions with respect to the elongate body 102. These can include the normal orientation (i.e., perpendicular to the elongate body surface) shown by arrows 109, as well as orientations directed proximally and distally along a longitudinal axis of the elongate body 102, including various orientations that develop a circular or spiral flow of liquid around the elongate body. Still further, in some embodiments, the elongate body 102 can be formed with an open distal end that serves as an outlet port. By way of example, in one embodiment, twenty-four equally-spaced outlet ports 108 having a diameter of about 0.4 mm can be created around the circumference of the electrode 105 using Electrical Discharge Machining (EDM). One skilled in the art will appreciate that additional manufacturing methods are available to create the outlet ports 108. In addition, in some embodiments, the outlet ports can be disposed along a portion of the elongate body adjacent to the electrode, rather than being disposed in the electrode itself.

The inner lumen 106 that communicates with the outlet ports 108 can also house a heating assembly 110 configured to heat fluid as it passes through the inner lumen 106 just prior to being introduced into tissue. The heating assembly 110 can have a variety of configurations and, in one embodiment, can include two wires suspended within the inner lumen 106. The wires can be configured to pass RF energy therebetween in order to heat fluid flowing through the inner lumen 106. In other embodiments, a single wire can be configured to pass RF energy between the wire and the inner walls of the elongate body. Further description of exemplary heating assemblies can be found in U.S. Pat. Pub. No. 2012/0265190, which is incorporated by reference above.

The portion of the elongate body located distal to the electrode 105 or other ablation element can be solid or filled such that the inner lumen 106 terminates at the distal end of the electrode 105. In one embodiment, the inner volume of the portion of the elongate body distal to the electrode can be filled with a plastic plug that can be epoxied in place or held by an interference fit. In other embodiments, the portion of the elongate body distal to the electrode can be formed from solid metal and attached to the proximal portion of the elongate body by welding, swaging, or any other technique known in the art.

The elongate body 102 illustrated in FIG. 1 can be configured for insertion into a patient's body in a variety of manners. FIG. 2 illustrates one embodiment of a medical device 200 having an elongate body 202 coupled to a distal end thereof and configured for laparoscopic or direct insertion into a target area of tissue. In addition to the elongate body 202, the device 200 includes a handle 204 to allow an operator to manipulate the device. The handle 204 includes one or more electrical connections 206 that connect various components of the elongate body (e.g., the heating assembly and ablation element 205) to, for example, the controller 118 shown in FIG. 1. The handle 204 also includes at least one fluid conduit 208 for connecting a fluid source to the device 200.

While the device 200 is one exemplary embodiment of a medical device that can be adapted for use in fluid enhanced ablation therapy, a number of other devices can also be employed. For example, a very small elongate body can be required in treating cardiac dysrhythmias, such as ventricular tachycardia. In such a case, an appropriately sized elongate needle body can be, for example, disposed at a distal end of a catheter configured for insertion into the heart via the circulatory system. In one embodiment, a stainless steel needle body between about 20- and about 30-gauge (i.e., an outer diameter of about 0.3 mm to about 0.9 mm) can be disposed at a distal end of a catheter. The catheter can have a variety of sizes but, in some embodiments, it can have a length of about 120 cm and a diameter of about 8 French ("French" is a unit of measure used in the catheter industry to describe the size of a catheter and is equal to three times the diameter of the catheter in millimeters).

Referring back to FIG. 1, an exemplary fluid source is shown as a fluid reservoir 112. The fluid reservoir 112 can have a variety of geometries and sizes. In one embodiment, the fluid reservoir 112 can be a cylindrical container similar to a syringe barrel that can be used with a linear pump, as described below. The fluid reservoir 112 can be connected to the inner lumen 106 via a fluid conduit 114 to supply fluid to the inner lumen and heating assembly 110. The fluid conduit 114 can be, for example, a length of flexible plastic tubing. The fluid conduit 114 can also be a rigid tube, or a combination of rigid and flexible tubing. A fluid used in the fluid reservoir 112 can be selected to provide the desired therapeutic and physical properties when applied to the target tissue, and a sterile fluid is recommended to guard against infection of the tissue. A preferred fluid for use in the SERF ablation technique is sterile normal saline solution (defined as a salt-containing solution). In the systems and methods described herein, an imageable fluid can be utilized and transformed into an imageable therapeutic fluid by heating the imageable fluid within the elongate body 102. An exemplary imageable fluid can include saline and a contrast agent to aid in visualizing the fluid. Regardless of what particular fluid is utilized, it can be important for the imageable therapeutic fluid to have a heat capacity that is equal to or greater than about ½ of the heat capacity of tissue to be treated during therapy. In one embodiment, the imageable therapeutic fluid can have a heat capacity that is equal to or great than about 2 J/ml-° C., and more preferably about 4 J/ml-° C. This is so the fluid can maintain its therapeutic effect as it exchanges thermal energy with the tissue. In some embodiments, for example, the contrast agent can be selected such that it does not significantly alter the heat capacity of the overall fluid (e.g., the contrast agent and saline) so as to maintain the therapeutic abilities of the imageable fluid.

Fluid can be urged from the fluid reservoir 112 into the inner lumen 106 by a pump 116. In one embodiment, the pump 116 can be a syringe-type pump that produces a fixed volume flow via linear advancement of a plunger (not shown). In other embodiments, however, other types of pumps, such as a diaphragm pump, may also be employed.

The pump 116, as well as any other components of the system, can be controlled by a controller 118. The controller 118 can include a power supply 119 and can be configured to deliver electrical control signals to the pump 116 to cause the pump to produce a desired flow rate of fluid. The controller 118 can be connected to the pump 116 via an electrical connection 120. The controller 118 can also include an interface for receiving lead wires or other connecting elements to electrically couple the controller 118 to the elongate body 102 and one or more return electrodes 124. These electrical connections, which can have any desired length and can utilize any known electrical connecting elements to interface with the controller 118 (e.g., plugs, alligator clips, rings, prongs, etc.), are illustrated in FIG. 1 as connections 122 and 126. In addition, the controller 118 can be connected to the heating assembly 110 through a similar electrical connection, as described below.

The return electrode 124 can have a variety of forms. For example, the return electrode 124 can be a single large electrode located outside a patient's body. In other embodiments, the return electrode 124 can be a return electrode located elsewhere along the elongate body 102, or it can be located on a second elongate body introduced into a patient's body near the treatment site. Regardless of the configuration used, the return electrode 124 is designed to receive current emitted from the mono-polar ablation element 105, thereby completing the circuit back to the controller 118 through the electrical connection 126.

In operation, the controller 118 can drive the delivery of fluid into target tissue at a desired flow rate, the heating of the imageable fluid to a desired therapeutic temperature, and the delivery of therapeutic ablative energy via the one or more ablation elements, such as electrode 105. To do so, the controller 118 can itself comprise a number of components for generating, regulating, and delivering required electrical control and therapeutic energy signals. In addition to the power supply 119 mentioned above, the controller 118 can include one or more digital data processors and associated storage memories that can be configured to perform a variety of functions, or control discrete circuit elements that perform a given function. These functions can include, for example, the generation of one or more electrical signals of various frequencies and amplitudes. Furthermore, the controller 118 can be configured to amplify any of these signals using one or more RF power amplifiers into relatively high-voltage, high-amperage signals, e.g., 50 volts at 1 amp. These RF signals can be delivered to the ablation element 105 via one or more electrical connections 122 and the elongate body 102 such that RF energy is passed between the emitter electrode 105 and any return electrodes or electrode assemblies 124 that are located remotely on a patient's body. In embodiments in which the elongate body is formed from non-conductive material, the one or more electrical connections 122 can extend through the inner lumen of the elongate body or along its outer surface to deliver current to the emitter electrode 105. The passage of RF energy between the ablation element and the return electrode 124 can heat the imageable therapeutic fluid and tissue surrounding the elongate body 102 due to their inherent electrical resistivity. The controller 118 can also include a number of other components, such as a directional coupler to feed a portion of the one or more RF signals to, for example, a power monitor to permit adjustment of the RF signal power to a desired treatment level. Still further, the controller 118 can include a user interface 121 to allow an operator to interact with the controller and set desired therapy operating parameters or receive feedback from the controller (e.g., warnings, indications, etc.).

As mentioned above, one challenge in fluid enhanced ablation therapy is monitoring the progress of the therapy. The ability to visualize the flow of a therapeutic fluid within a patient's body can be important for several reasons. For example, visualizing the flow can provide an indication of how much of a target tissue volume has received, or is likely to have received, a therapeutic dose of thermal energy from the treatment therapy. In addition, visualizing the flow of such a fluid can be helpful for an operator to determine if the elongate body is correctly positioned within a patient's body and whether or not the fluid is flowing within the target treatment volume in an expected manner.

Prior art techniques for monitoring the progress of fluid enhanced ablation therapy largely focus on measuring the temperature of tissue at specific points within the target tissue volume. Exemplary embodiments of such techniques are described in U.S. Pat. Pub. No. 2012/0277737, incorporated by reference above. Measuring the temperature of specific locations within a target tissue volume is not necessarily an effective indication of therapy process. In particular, sensors report only the temperature at their specific location, and do not provide information on the development of the volume of treated tissue as a whole. In addition, in the event that unexpected fluid flow is encountered (e.g., due to an adjacent vein or other anatomical feature that draws fluid away from the target tissue volume), remote temperature sensors might not provide any meaningful information other than the absence of an increase in temperature within the target tissue volume.

The systems and methods of the present invention address these challenges by providing for the direct visualization of the flow of a therapeutic fluid within a patient's body. This is accomplished by using an imageable fluid that can be viewed using any of a variety of known medical imaging technologies including, for example, fluoroscopy, computed tomography (CT) scanning, computer axial tomography (CAT) scanning, magnetic resonance imaging (MRI), and ultrasound. Furthermore, the systems and methods described herein allow for the determination of the size of a tissue volume that has received a therapeutic dose of thermal energy based on the size of a tissue volume that contains the imageable therapeutic fluid. The relationship between the sizes of these tissue volumes can be 1:1, or some other value based on the tissue type and therapy parameters in use, as described in more detail below.

In one aspect, for example, a method for ablating tissue is provided that includes inserting into a tissue volume an elongate body having an ablation element disposed thereon. The method can further include heating an imageable fluid within the elongate body to transform the imageable fluid into an imageable therapeutic fluid, and delivering energy to the ablation element on the elongate body. The energy and the imageable therapeutic fluid can be simultaneously delivered into the volume of tissue to deliver a therapeutic dose of thermal energy. The method can further include imaging the tissue volume to determine the extent of the tissue volume containing the imageable therapeutic fluid, wherein the imageable therapeutic fluid indicates the extent of the tissue volume that has received the therapeutic dose of thermal energy.

Figure 3A:
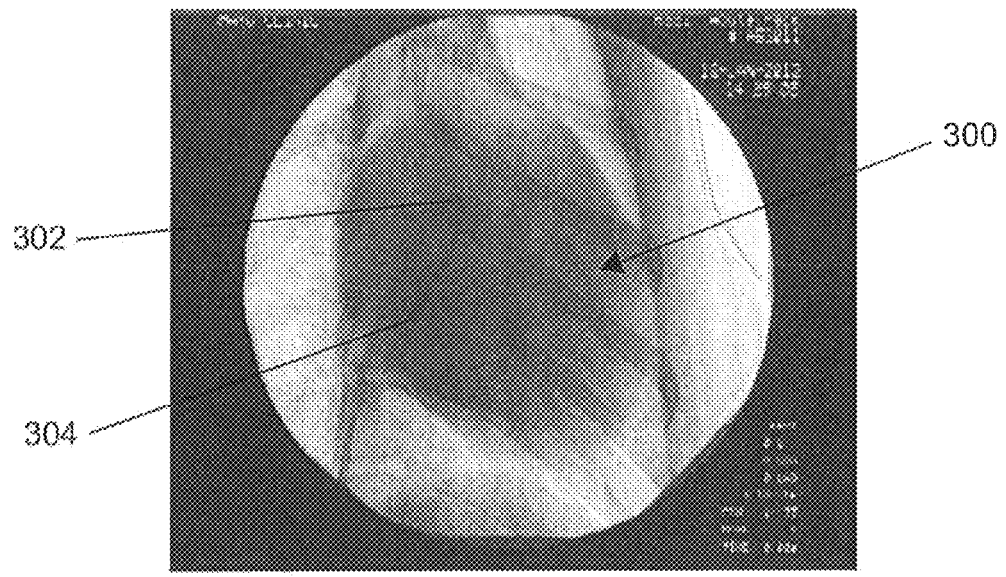
FIG. 3A is a fluoroscopic X-ray image of a fluid enhanced ablation therapy device disposed in a heart prior to therapy.
Figure 3B:
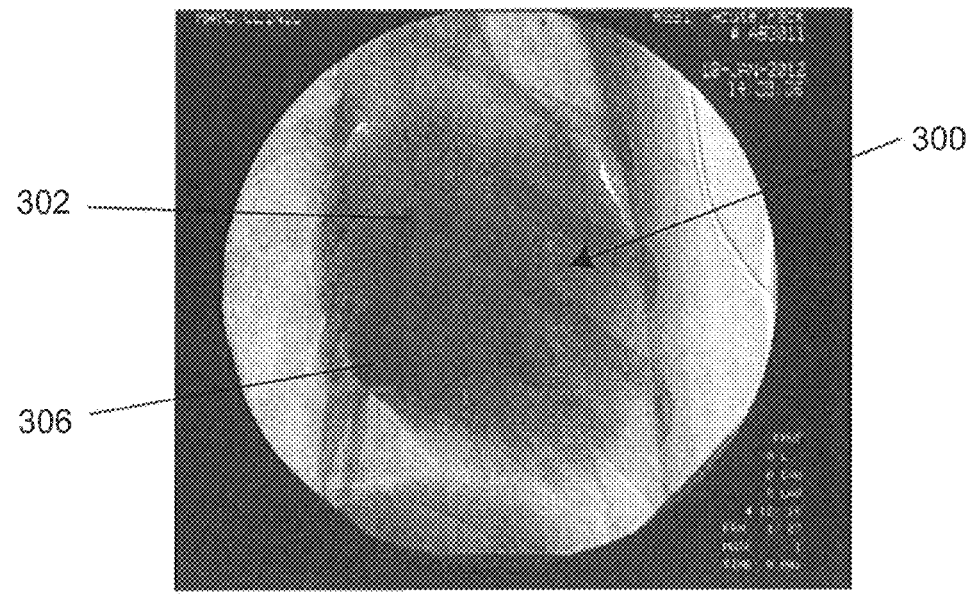
FIG. 3B is an fluoroscopic X-ray image of the fluid enhanced ablation therapy device of FIG. 3A during therapy.

FIGS. 3A-3B illustrate one embodiment of such a method. FIG. 3A, in particular, is an X-ray image of a heart 300 taken prior to the commencement of fluid enhanced ablation therapy. Visible within the heart is a catheter 302 having a needle body disposed at a distal end 304 thereof. FIG. 3B is an X-ray image of the heart 300 taken at a point during fluid enhanced ablation therapy. Visible in FIG. 3B is an imageable therapeutic fluid 306 surrounding and obscuring the distal end 304 of the catheter 302. The imageable therapeutic fluid 306 is being introduced into the heart 300 from the needle body disposed at the distal end 304 (not shown in FIG. 3B) of the catheter 302. By monitoring the heart 300 using X-rays, the imageable therapeutic fluid 306 can be directly visualized to determine if the fluid is flowing through the tissue of the heart in an expected manner. Furthermore, the extent of the heart tissue containing the imageable therapeutic fluid 306 can be used to indicate the extent of the heart tissue that has received a therapeutic dose of thermal energy.

Figure 4:
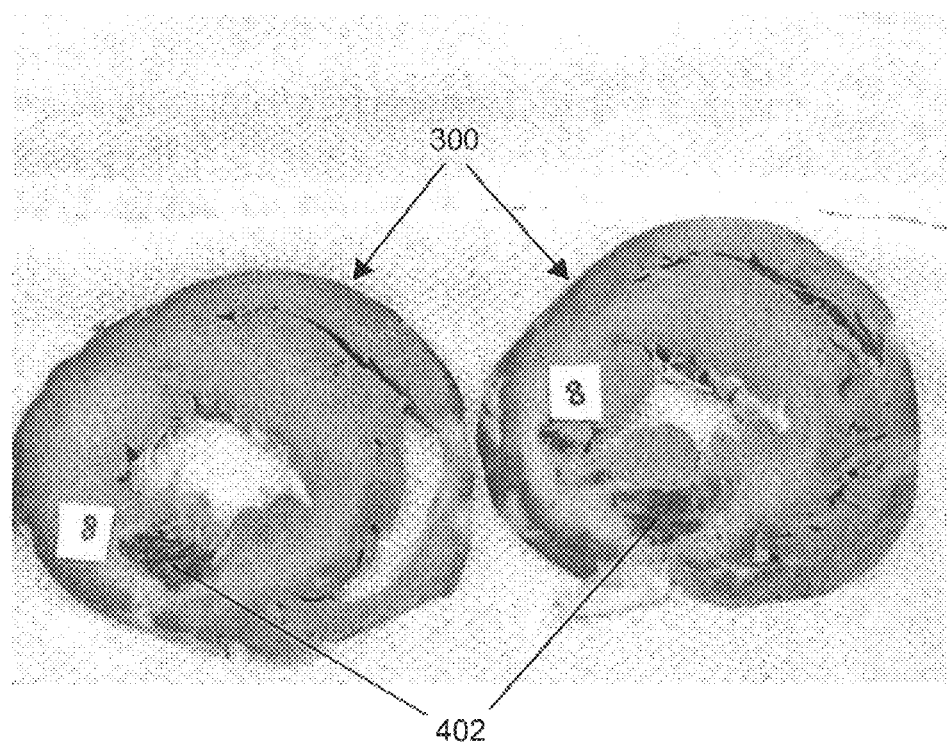
FIG. 4 is an image of the heart of FIGS. 3A-3B after therapy.

FIG. 4 illustrates cross-sectional slices of the heart 300 taken after completion of the therapy shown in FIGS. 3A-3B. Visible in the figure is a lesion 402 formed during the fluid enhanced ablation therapy procedure. The size of the lesion 402 corresponds to the size of the imageable therapeutic fluid 306 visible in FIGS. 3A-3B, as the imageable therapeutic fluid 306 remained within a treated volume of tissue only, or at least within a volume of tissue that can be correlated with a treated volume of tissue, for a duration of time sufficient to capture an image of where the imageable therapeutic fluid has flowed. The properties of the imageable therapeutic fluid used can affect the ability of the flow to be visualized. For example, if an imageable therapeutic fluid includes a contrast agent (or other compound to enable visualization of the fluid) that has too small of a molecular weight, the fluid can dissipate too quickly in the vasculature or throughout the tissue to provide useful visualization. Conversely, if the contrast agent or other compound has too large of a molecular weight, it can be filtered by the spaces in the extracellular fluid, which can result in the contrast agent being separated from the other components of the imageable therapeutic fluid. This can effectively make imaging of the therapeutic fluid impossible.

As described above, different fluids can be used in fluid enhanced ablation therapy and, accordingly, the imageable fluid can also include a variety of different fluids. In some embodiments, for example, the imageable fluid can be saline (or one or more other fluids used in place of saline) in combination with a contrast agent that can aid in visualizing the flow of the fluid. A contrast agent can be any substance that can be more easily detected using any of a variety of medical imaging technologies. For example, in the case of fluoroscopy and other X-ray medical imaging technologies, a contrast agent can be a fluid having a higher (e.g., positive) Hounsfield Unit value than the saline or other fluids being used. The Hounsfield Unit is a measurement of radiodensity in which a higher positive number indicates a greater ability to absorb, e.g., X-rays.

Furthermore, and as described above, a contrast agent can be selected such that the mixture of the contrast agent and other fluids (e.g., saline) does not have a significantly different heat capacity than the other fluids alone. Still further, the heat capacity of the mixture can be close to, or greater than, the heat capacity of the tissue to be treated. This can be important because a therapeutic fluid having a significantly lower heat capacity than the surrounding tissue can negatively affect the therapy. Accordingly, the imageable components of the imageable therapeutic fluid can, in some embodiments, be selected such that they are not filtered within the tissue volume, do not dissipate too rapidly within the tissue volume, do not interfere with the heating element within the elongate body, and further do not negatively affect the therapeutic performance of the fluid once in tissue.

There are many contrast agents known in the art, but one of ordinary skill in the art would not think to use them in combination with fluid enhanced ablation therapy for a number of reasons. For example, any contrast agent used in fluid enhanced ablation must be stable at the elevated therapeutic temperatures encountered during therapy. Many known contrast agents are not stable at these elevated temperatures (e.g., above 40° C.) and actually can become poisonous when raised to such elevated temperatures. Furthermore, many known contrast agents are non-ionic substances. This can raise concerns about whether the presence of the non-ionic contrast agent might interfere with, for example, the conduction of electrical energy between the ablation element and the ionic saline, saline solution, or other therapeutic fluid. Still further and as mentioned above, many contrast agents are large-molecule substances that may not be able to flow through the extracellular space of a volume of tissue due to the size of the molecules. If the contrast agent cannot flow with the saline through the extracellular space of the target tissue volume, it cannot serve its purpose of aiding to visualize the flow of fluid through the volume.

The systems and methods of the present invention can make use of any contrast agent that satisfies the criteria discussed above. One such contrast agent utilized in certain embodiments is iohexol, a non-ionic dye that is stable at the elevated temperatures encountered during fluid enhanced ablation therapy, does not negatively affect the transfer of energy between the ablation element and the imageable fluid, and has a sufficiently small molecular size to pass through the extracellular space of human tissue. The iohexol can be added directly to the saline, or it can be mixed in solution first prior to being mixed with the saline. The iohexol contrast solution is commercially available under the trade name Omnipaque®, manufactured by GE Healthcare. Note that spreading of a dye contrast agent like iohexol via chemical diffusion is not generally a concern because diffusion takes much longer than convection. As a result, over the time periods typically used in fluid enhanced ablation therapy, it can be assumed that the presence of a dye contrast agent is due to convective fluid flow, not chemical diffusion.

A suitable contrast agent can be mixed with saline or one or more other fluids in a variety of ratios. For example, in the embodiment illustrated in FIGS. 3A-3B, the contrast agent iohexol was mixed with saline in a 1:1 ratio. In other embodiments, however, a ratio between saline and a contrast agent can be about 10:1, about 20:1, about 50:1, or even greater. The amount of contrast agent added to saline need only be large enough to have the desired effect of enabling the flow of the imageable therapeutic fluid to be viewed when using a medical imaging technology. Furthermore, a number of different medical imaging technologies can be utilized to visualize the flow of fluid within the target tissue volume, and certain of these technologies can require the use of different contrast agents. For example, suitable medical imaging technologies for use in the systems and methods described herein can include X-ray imaging, fluoroscopy, computed tomography (CT) scan, computer axial tomography (CAT) scan, magnetic resonance imaging (MRI), and ultrasound, and contrast agents suitable for use with one or more of these technologies may not be suitable for use with others.

The contrast agent can be mixed with the saline in a variety of manners. For example, with reference to FIG. 1, in some embodiments the contrast agent can be pre-mixed with the saline or other appropriate fluid within the fluid reservoir 112. The quantity of contrast agent can be preselected based on the volume of saline present in the fluid reservoir 112, and the fluids can be mixed before use to ensure even dispersion of the contrast agent within the fluid reservoir.

Figure 5:
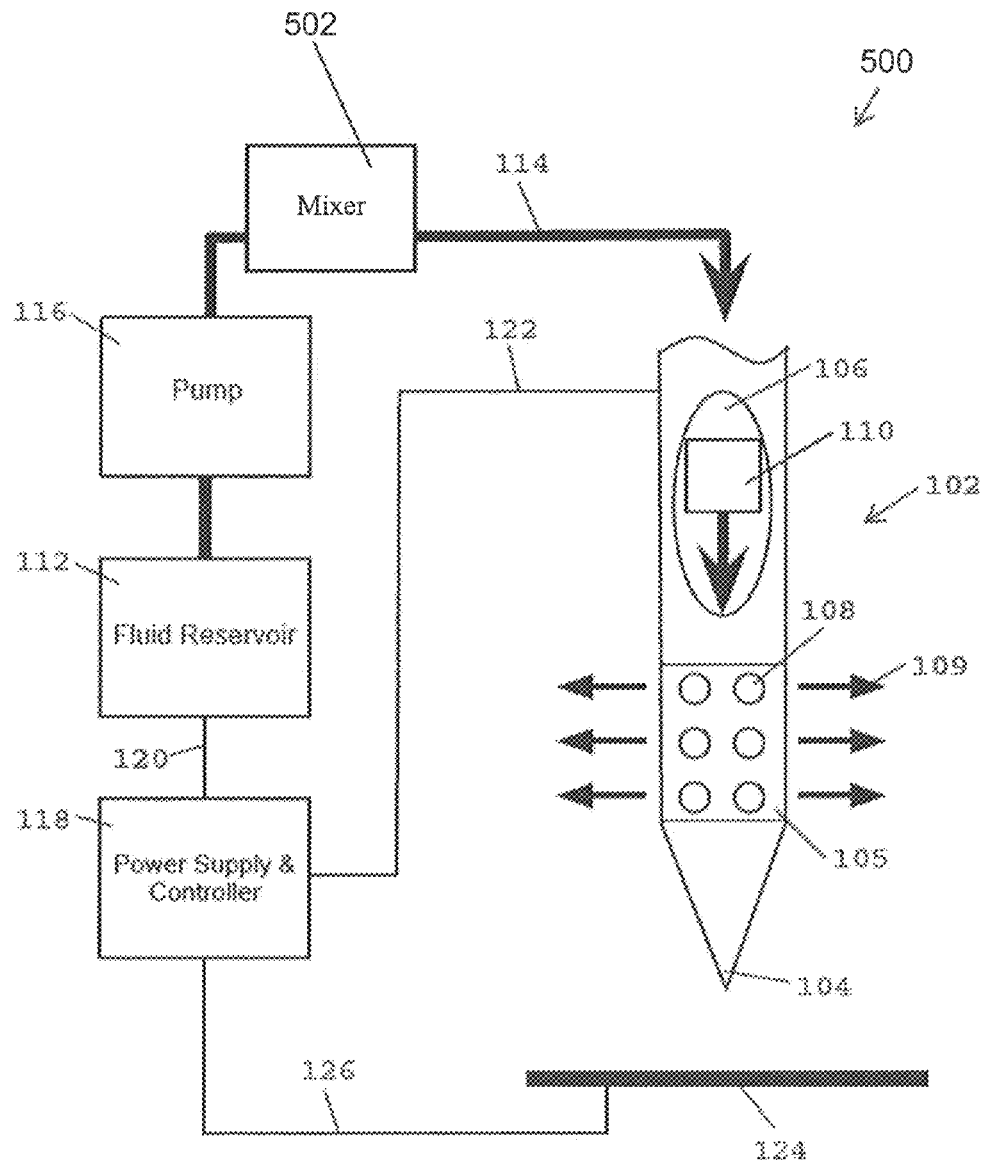
FIG. 5 is an alternative embodiment of a fluid enhanced ablation therapy system.

FIG. 5 illustrates an alternative embodiment for introducing a contrast agent into saline or another appropriate fluid during fluid enhanced ablation therapy. The system 500 includes all of the same components as the system 100 of FIG. 1, but further includes a mixer 502 disposed inline with the fluid reservoir 112 and pump 116. The mixer 502 can be configured to inject into the fluid flowing through the conduit 114a predetermined amount of contrast agent such that the desired ratio of saline to contrast agent is achieved as the imageable fluid exits the outlet ports 109 of the elongate body 102. One skilled in the art will appreciate that other mechanisms for introducing a contrast agent into a reservoir or flow of liquid are possible and these are also considered within the scope of the invention.

As described above, the systems and methods described herein not only provide for the direct visualization of the extent of a tissue volume containing an imageable therapeutic fluid, but also for the determination of the extent of the tissue volume that has received a therapeutic dose of thermal energy based on the visualization of the fluid flow. The relationship between the size of the volume of tissue containing the imageable therapeutic fluid and the size of the volume of tissue that has received a therapeutic dose of thermal energy can vary depending on a number of factors, including the definition of a therapeutic dose, the therapy operating parameters, the tissue type and other anatomical features, etc. In some embodiments, for example, a ratio between a linear dimension of the tissue volume containing the imageable therapeutic fluid and a linear dimension of the tissue volume that has received the therapeutic dose of thermal energy can be about 1:1. This proportion can be approached when the heat capacity of the imageable therapeutic fluid is much greater than that of the tissue. In other embodiments, however, the ratio can be smaller, indicating that only a portion of the volume containing the imageable therapeutic fluid has received a therapeutic dose of thermal energy. For example, in some embodiments, the ratio between a linear dimension of the tissue volume containing the imageable therapeutic fluid and a linear dimension of the tissue volume that has received the therapeutic dose of thermal energy can be about 3:2. In other embodiments, the ratio can be about 2:1, about 5:1, or about 10:1.

Figure 6:
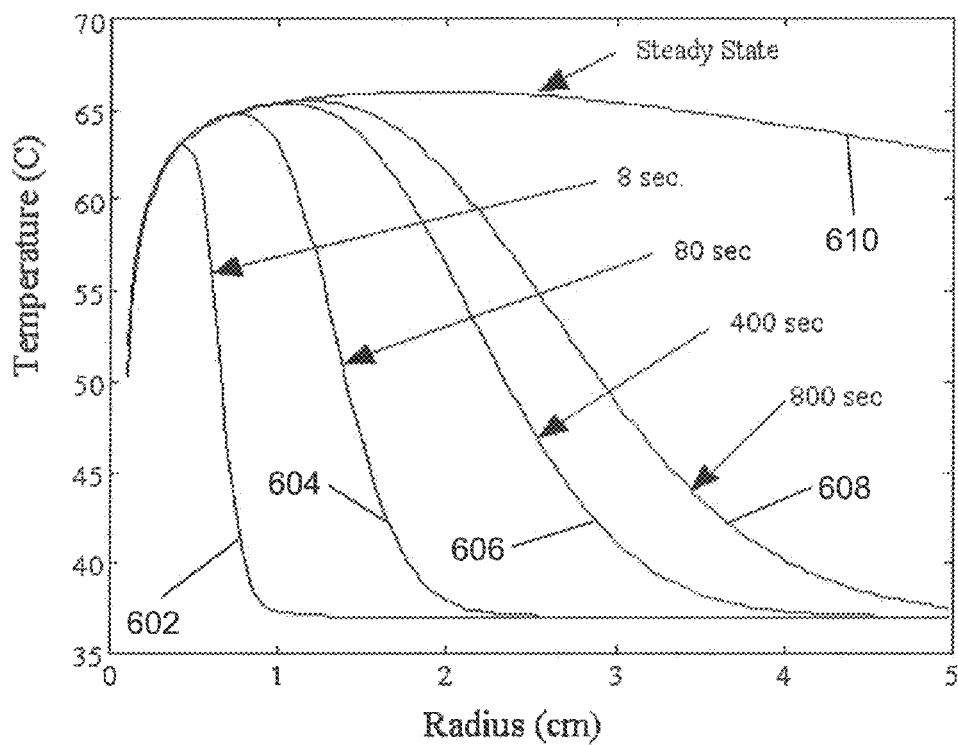
FIG. 6 is a graphical representation of simulated fluid enhanced ablation therapy heating profiles over time.

There are a number of different methods for calculating a therapeutic thermal dose, and any calculation ultimately depends on the temporal history of temperature (i.e., the amount of heating the tissue has previously endured) and the type of tissue being heated. Nonetheless, one exemplary suggestion by Nath, S. and Haines, D. E., *Prog. Card. Dis.* 37(4):185-205 (1995) (Nath et al.) is that raising the temperature of tissue to 50° C. for one minute administers a therapeutic dose and destroys the tissue. FIG. 6 illustrates simulated temperature profiles of a spherical volume of tissue extending away from a centrally-located elongate body at various times after the initiation of fluid enhanced ablation therapy. To create the simulated profiles shown in FIG. 6, an RF power output of 25 Watts with 10 ml/min flow of 50° C. saline was assumed.

Using the exemplary 50° C. mark as indicative of delivery of a therapeutic dose, the expansion of the treated volume of tissue can be seen over time. In particular, the first profile 602, taken 8 seconds after the initiation of therapy, indicates that the volume of tissue that has received a therapeutic dose of thermal energy extends less than 1 cm from the elongate body delivering the heated saline and RF or other energy. By 80 seconds after the initiation of therapy, the radius of the treated tissue volume extends about 1.5 cm from the elongate body, as shown by profile 604. The third profile 606, taken 400 seconds after initiating therapy, shows the therapeutic dose has been administered to a volume extending about 2.5 cm from the elongate body. The fourth profile 608, taken 800 seconds after initiating therapy, indicates that the therapeutic dose has been administered to a volume of tissue extending about 3 cm from the elongate body. The final profile 610 shows a steady state temperature profile indicating that over a longer period of time a treatment volume can grow to extend well over 5 cm from the elongate body.

As mentioned above, the expansion over time of a proportion of a volume of tissue that contains an imageable therapeutic fluid can be equal to or faster than the expansion of the 50°+ C. isotherm shown in FIG. 6, depending on a number of different factors. For example, in an embodiment utilizing a contrast agent such as iohexol, it is known that the contrast agent will preferentially travel through the extracellular space and will only slowly enter the cells themselves. The imageable therapeutic fluid, on the other hand, will exchange thermal energy with both the extracellular space and the cells themselves. In the liver, for example, the extracellular space comprises approximately ⅓ of the volume of tissue in the organ. Accordingly, if a volume of therapeutically heated saline is delivered at a flow rate Q for a time t, the imageable fluid can fill a volume V approximately 3 times larger (because it travels through only ⅓ the space of the saline), but the thermal energy will be exchanged with the entire volume of tissue that the imageable therapeutic fluid has flowed through. Using this information, in combination with the model used to create the temperature profiles of FIG. 6, a relationship between a radius of the volume containing the imageable fluid and a radius of the volume that has received a therapeutic dose of thermal energy can be determined.

The radius of the volume of tissue that the imageable therapeutic fluid has flowed through can be expressed in terms of Qt. To begin, the volume of tissue that the injected imageable therapeutic fluid has filled, V, is:

$$V = 3Qt \tag{1}$$

Further, the imageable radius r is related to the filled volume according to:

$$V = \frac{4}{3}\pi r^3 \tag{2}$$

The imageable radius r is therefore:

$$r = \sqrt[3]{\frac{9}{4\pi}Qt} \tag{3}$$

This equation can be used to solve for the radius r of a volume containing a contrast agent at any time t given a fluid flow rate Q.

Figure 7:
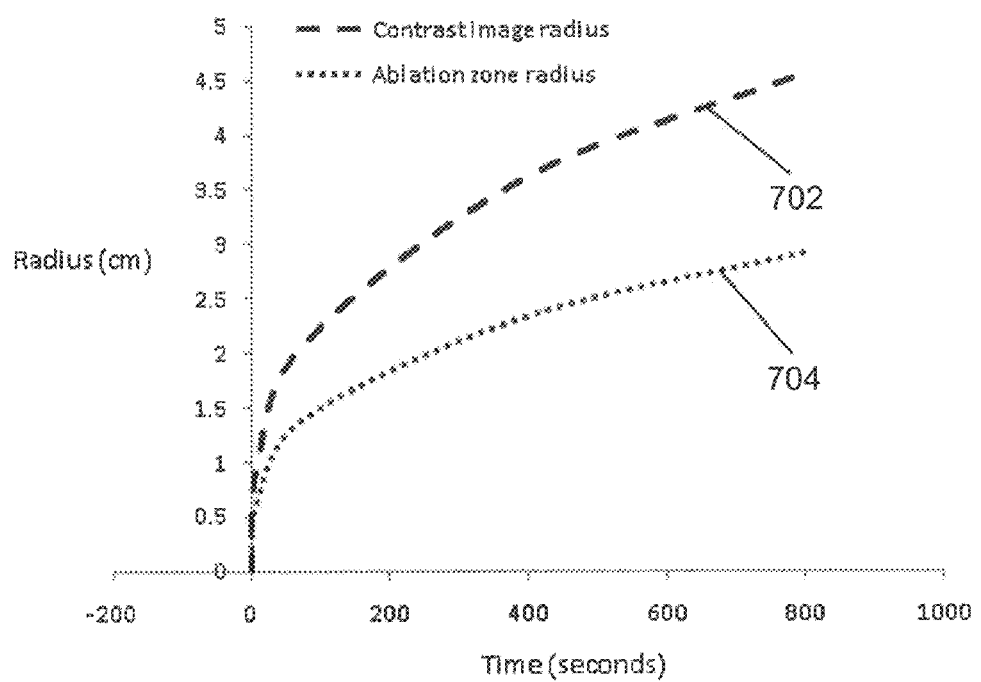
FIG. 7 is a graphical representation of simulated expansion over time of a proportion of a tissue volume that contains contrast agent and a proportion of the tissue volume that has received a therapeutic dose of thermal energy.

Using the therapy parameters for the temperature profiles shown in FIG. 6, FIG. 7 plots the expansion over time of the radius of the volume containing imageable therapeutic fluid and the radius of the volume having received a therapeutic dose of thermal energy. In particular, the dashed line 702 indicates the radius of the volume containing imageable therapeutic fluid from the initiation of therapy out to approximately 800 seconds. The dotted line 704 indicates the radius of the volume having received a therapeutic dose of thermal energy over the same time period. As is evident from the figure and can be confirmed using the mathematical model developed above, the radius of the volume having received a therapeutic dose of thermal energy is about ⅔ the radius of the volume containing imageable therapeutic fluid.

Thus, in this example, a ratio of a linear dimension of the volume of tissue containing imageable therapeutic fluid to a linear dimension of the volume of tissue that has received a therapeutic dose of thermal energy is about 3:2. Of course, this is just one possible ratio based on the heat capacity of the imageable therapeutic fluid, shape of the tissue volumes, type of tissue being treated, and therapy parameters. The ratios can vary based on differences in any of these parameters, but the concept remains the same, i.e., the expansion of an imageable fluid can be visualized and the size of a therapeutically treated volume of tissue can be determined based on the visualization.

Another advantage of the systems and methods described herein is the ability for a user to determine if the fluid being introduced into the target volume of tissue is flowing in an expected manner. If unexpected fluid flow is observed, a user can terminate therapy to diagnose the cause, reposition the elongate body, etc. The ability to actively monitor the development of a treatment volume and the flow of a therapeutic fluid within a patient's body can thus improve the safety of fluid enhanced ablation therapy.

For example, there are a number of situations in which incorrect placement of a needle or other elongate body can result in undesired fluid flow. In the liver, for example, incorrect placement of an elongate body or use of a high fluid flow rate can cause a hydro-dissection of the liver tissue in which the flowing saline tears the tissue apart rather than flow through the extracellular space. In addition, it is undesirable for fluid to flow out of the liver into the abdominal space. Each of these undesired phenomena can be directly visualized using the systems and methods of the present invention unlike prior art methods for monitoring fluid flow. Moreover, direct visualization allows for improved speed and accuracy during therapy delivery.

Fluid enhanced ablation therapy is also used commonly in the heart to treat cardiac dysrhythmias, such as ventricular tachycardia. Similar to the liver, misplacement of the elongate body in the heart can result in potentially dangerous undesired fluid flow. For example, if the elongate body extends too far and passes through the ventricular wall of the heart, fluid can be introduced into the space between the ventricle wall and pericardial sac. Further, this kind of positioning error can be common because the walls of the heart have varying thicknesses depending on location. Being able to visualize the flow of fluid introduced into the heart, liver, or other area of the body can allow for rapid recognition of undesired fluid flow and enable subsequent remedial steps to correct the flow and resume therapy.

By way of further example, undesired flow can occur even when the elongate body is correctly positioned in a volume of tissue due to the presence of certain anatomical structures. Veins, capillaries, and other sources of blood flow, for example, can carry fluid introduced adjacent thereto away from the target treatment volume of tissue, thereby preventing the tissue in the target volume of tissue from being raised to a therapeutic level. Directly visualizing the flow of fluid introduced into the patient's body can alert a user to the presence of such an anatomical feature quickly and allow for more rapid resumption of therapy after repositioning or otherwise compensating for the adjacent blood flow (e.g., by increasing fluid temperature or flow rate).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A method for ablating tissue, comprising:
   inserting an elongate body into a tissue volume where about ⅓ of the volume is extracellular space;
   heating a fluid within the elongate body that contains saline and a contrast agent that can be viewed using an X-ray imaging technology;
   delivering the heated fluid into the tissue volume through an outlet port formed in the elongate body;
   delivering energy into the tissue volume from an ablation element disposed on the elongate body simultaneously with the heated fluid;
   capturing an image of the tissue volume using the X-ray imaging technology, wherein the image shows a substantially circular portion of the tissue volume containing the contrast agent of the heated fluid and centered about the outlet port;
   computing with a digital data processor a first radius of the substantially circular portion of the tissue volume containing the contrast agent of the heated fluid based on the captured image;
   computing with a digital data processor a second radius that is about ⅔ of the first radius, wherein the second radius represents a portion of the tissue volume that has received a dose of thermal energy sufficient to destroy tissue; and
   halting delivery of at least one of the heated fluid and energy when the second radius reaches a predetermined value.

2. The method of claim 1, wherein a heat capacity of the fluid is greater than about 2 J/ml-° C.

3. The method of claim 1, wherein the fluid comprises saline and a contrast agent.

4. The method of claim 3, wherein a ratio of the saline to the contrast agent is about 1:1.

5. The method of claim 3, wherein a ratio of the saline to the contrast agent is about 10:1.

6. The method of claim 3, wherein a ratio of the saline to the contrast agent is about 20:1.

7. The method of claim 3, wherein the contrast agent is iohexol.

8. The method of claim 1, wherein the fluid is heated by a heating element disposed within the elongate body.

9. The method of claim 1, wherein the ablation element comprises a source of electromagnetic energy.

10. The method of claim 9, wherein the electromagnetic energy is RF electrical energy.

11. The method of claim 9, wherein the electromagnetic energy is laser light energy.

12. The method of claim 9, wherein the electromagnetic energy is microwave electrical energy.

13. The method of claim 1, wherein the ablation element comprises a source of ultrasonic energy.

14. The method of claim 3, wherein the fluid includes a greater amount of saline than contrast agent.

15. The method of claim 3, wherein a ratio of the saline to the contrast agent is about 50:1.

16. The method of claim 3, wherein a ratio of the saline to the contrast agent is about 200:1.

17. A method for ablating tissue, comprising:
   inserting an elongate body into a liver of a patient;
   delivering a fluid including a contrast agent into the target volume of tissue from an outlet port formed in an elongate body, wherein the fluid is heated prior to being delivered into the target volume of tissue, and simultaneously delivering energy into the target volume of tissue from an ablation element adjacent to the elongate body;
   capturing an image of the target volume of tissue with an X-ray imaging technology that shows a substantially circular portion of the target volume of tissue that contains the contrast agent centered about the outlet port;
   computing with a digital data processor a first radius of the substantially circular portion of the target volume of tissue that contains the contrast agent based on the captured image;
   computing with a digital data processor a second radius that is about ⅔ of the first radius, wherein the second radius represents a portion of the tissue volume that has received a dose of thermal energy sufficient to destroy tissue; and
   stopping delivery of the fluid and the energy into the target volume of tissue when the second radius reaches a predetermined size.

* * * * *